(12) United States Patent
Petkovic et al.

(10) Patent No.: US 9,892,279 B2
(45) Date of Patent: Feb. 13, 2018

(54) CREATING AN ACCESS CONTROL POLICY BASED ON CONSUMER PRIVACY PREFERENCES

(75) Inventors: Milan Petkovic, Eindhoven (NL); Vojkan Mihajlovic, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 245 days.

(21) Appl. No.: 13/997,276

(22) PCT Filed: Dec. 14, 2011

(86) PCT No.: PCT/IB2011/055669
§ 371 (c)(1),
(2), (4) Date: Jun. 24, 2013

(87) PCT Pub. No.: WO2012/085767
PCT Pub. Date: Jun. 28, 2012

(65) Prior Publication Data
US 2013/0312060 A1 Nov. 21, 2013

(30) Foreign Application Priority Data
Dec. 22, 2010 (EP) .................................... 10196417

(51) Int. Cl.
*G06F 7/04* (2006.01)
*G06F 21/62* (2013.01)
(Continued)

(52) U.S. Cl.
CPC .... *G06F 21/6245* (2013.01); *G06F 17/30675* (2013.01); *G06F 19/322* (2013.01); *G06Q 50/22* (2013.01)

(58) Field of Classification Search
CPC ......... G06F 21/6245; G06F 2221/2141; G06F 17/30734; G06F 21/10; G06F 21/31;
(Continued)

(56) References Cited

U.S. PATENT DOCUMENTS 7,711,749 B2 5/2010 Brodie et al.
2004/0172307 A1 9/2004 Gruber
(Continued)

FOREIGN PATENT DOCUMENTS

CN 1284185 A 2/2001
JP H1018742 A 1/1998
(Continued)

OTHER PUBLICATIONS

Jin, J. et al., "Patient-centric Authorization Framework for Sharing Electronic Health Records". SACMAT '09 Proceedings of the 14th ACM symposium on access control models and technologies. Jun. 3-5, 2009, pp. 125-134. ACM NY.
(Continued)

*Primary Examiner* — Kendall Dolly
*Assistant Examiner* — Carlton Johnson

(57) ABSTRACT

A system for generating an access control policy comprises a user interface (1) for enabling a user to indicate a topic (10) and a set of permissions (15). A document analyzer (2) analyzes the content of a plurality of documents (11) to find a set of documents (13) relating to the topic (10). A property finder (5) analyzes the content of a plurality of documents (11) to find at least one distinguishing property (12) of documents relating to the topic (10). A document selector (6) selects the set of documents (13), based on the distinguishing property (12). An associating subsystem (3) associates the set of permissions (15) with the set of documents (13) to obtain an access control policy (4).

13 Claims, 5 Drawing Sheets

(51) Int. Cl.
  *G06F 17/30*  (2006.01)
  *G06Q 50/22*  (2012.01)
  *G06F 19/00*  (2011.01)

(58) Field of Classification Search
  CPC ....... H04L 63/20; H04L 63/10; H04L 63/102; H04L 63/0263
  See application file for complete search history.

(56) References Cited

U.S. PATENT DOCUMENTS

| | | |
|---|---|---|
| 2007/0150315 A1 | 6/2007 | Bennett et al. |
| 2009/0055431 A1* | 2/2009 | Brodie et al. ............ 707/103 R |
| 2009/0144255 A1 | 6/2009 | Chow et al. |

FOREIGN PATENT DOCUMENTS

| | | |
|---|---|---|
| JP | 2001067323 A | 3/2001 |
| JP | 2005302042 A | 10/2005 |
| JP | 2007299093 A | 11/2007 |
| JP | 2008299518 A | 12/2008 |
| JP | 2009134714 A | 6/2009 |
| JP | 200946345 A | 7/2009 |

OTHER PUBLICATIONS

Baeza-Yates, R. et al. "Modern Information Retrieval". (1999) Essex, UK: ACM Press.

Rasolofo, Y. et al. "Term Proximity Scoring for Keyword-Based Retrieval Systems". Published in Lecture Notes in Computer Science 2633, 1611-3349, 2003.

Liu, Y. et al. "Building a controlled health vocabulary in Japanese". Method Inform Med Apr. 2001, pp. 307-314.

Amer-Yahia, S. "Storage Techniques and Mapping Schemas for XML", Published by ACM in 2003. AT&T Labs Research.

Steele, R. et al. "HeathPass: Fine-grained Access Control to Portable Personal Health Records". 2010 24th IEEE International Conference on Advanced Information Networking and Applications.

Simons, W. et al. "The PING Personally Controlled Electronic Medical Record System: Technical Architecture". Journal of the American Medical Informatics Association, vol. 12, No. 1, Jan./Feb. 2005.

Hettne, K. et al. "Rewriting and suppressing UMLS terms for improved biomedical term identification". Journal of Biomedical Semantics 2010, 1:5.

* cited by examiner

CREATING AN ACCESS CONTROL POLICY BASED ON CONSUMER PRIVACY PREFERENCES

FIELD OF THE INVENTION

The invention relates to creating an access control policy. The invention further relates to configuring an access control system with an access control policy.

BACKGROUND OF THE INVENTION

Electronic health records, as well as electronic personal health records, have been increasingly used to replace paper records in professional healthcare and home healthcare.

Informed consent is a very important process in professional healthcare, in which the patient makes some choices with respect to, inter alia, the use of his health data by healthcare providers. In many countries the patient has legal rights to hide or limit access to certain parts of his electronic healthcare records. For example, a patient may restrict access to documents relating to mental health or drug abuse, such that only the patient's psychiatrist has access to these documents. In another example, such restricted access prevents others from having access to a patient's records related to AIDS. Different security mechanisms have been developed to technologically facilitate this right, such as the use of sealed envelopes in the Spine system of NHS in the UK or a similar mechanism in the NICTIZ system in The Netherlands.

In the domain of personal health records, the patient is solely responsible for defining who has access to his records. Very often the patient has a desire to realize a very complex policy, especially in the case that the patient wants to give access to certain healthcare providers, family or friends. In some cases, the patient might want to block them from being able to access certain parts of his/her records.

HL-7, IHE and HITSP standardize interactions related to patient consent as well as formats in which consent can be specified. HL-7 specifies CDA R2 consent directive, while IHE developed Basic Privacy Patient consent profile. The privacy preference working group of HITSP collected requirements related to the patient privacy preferences in respect of health records. HL-7 also standardized vocabularies used for access control, such as an object vocabulary that describes different data types of electronic health records. These data types are used by the access control system, which assigns permissions/restrictions to different users with respect to these data types.

"Patient-centric authorization framework for sharing electronic health records", Jing Jin et al., SACMAT'09, Jun. 3-5, 2009, Stresa, Italy, discloses a need for a secure, usable, and straightforward mechanism that allows users to quickly and easily authorize a variety of medical affiliates to access their sensitive records or a subset of the data within them. The paper discloses a model in which the semantics and structural composition of EHR documents is formulated in a hierarchical structure, where internal sub-objects are distinguished and associated with properties to address important criteria for medical data sharing such as data types, intended purposes and information sensitivities. Both the EHR instances and the aggregated virtual composite EHR are uniformly modelled as a labelled hierarchical structure. Relevant properties are categorized into three dimensions: origin, sensitivity, and object type.

SUMMARY OF THE INVENTION

It would be advantageous to have an improved system for creating an access control policy. To better address this concern, a first aspect of the invention provides a system comprising a user interface for enabling a user to indicate a topic and a set of permissions;

a document analyzer for analyzing the content of a plurality of documents to find a set of documents relating to the topic; and an associating subsystem for associating the set of permissions with the set of documents to obtain an access control policy.

Because the system takes into account the content of the plurality of documents, the system is able to more accurately determine the set of documents to which the user intends to apply the set of permissions. This may provide a better result than an approach which only takes into account the structure or a global classification of the documents or records. The user may be more confident that the topic is translated well into a set of documents which relate to the topic. Moreover, it becomes easier for the user to create a fine-grained access control policy, because the user is less concerned with any hierarchical structure in which documents are stored, and thus the user needs to know fewer details of the structure of the information system.

The document analyzer may comprise a property finder for analyzing the content of a plurality of documents to find at least one distinguishing property of documents relating to the topic. The document analyzer may further comprise a document selector for selecting the set of documents, based on the distinguishing property. The property finder helps to improve the selection of the relevant documents. By finding a distinguishing property of the documents relating to the topic, it becomes possible to select the set of documents by searching for documents having that property. By virtue of the analysis of the content of documents to find a distinguishing property, it is not necessary to define all possible properties of all possible topics beforehand, which would be a labor-intensive and error-prone job. Moreover, the property finder may give more reliable results in an environment where the topics and properties of documents relating thereto are subject to change. Moreover, in many cases, it is not feasible to define a general template for a specific topic, as each instance of records might be different. For example, it may be problematic to identify in advance all possible data types of an electronic health record in which information about AIDS in the case of a particular AIDS patient can be stored. Therefore a solution that can find them during runtime is preferred.

The document analyzer may comprise a document pre-selector for selecting the plurality of documents that are analyzed by the property finder, based on the topic. This helps to determine the plurality of documents. For example, the document pre-selector selects a plurality of documents relating to the topic. Such selection may be performed by matching of the document type with the topic, or by analyzing the content of documents and selecting documents whose content contains one or more words relating to the topic.

The document analyzer may comprise a data type selector for selecting at least one data type, based on the topic. The document pre-selector may be arranged for selecting a plurality of documents of the selected data type. This is an efficient way to find a plurality of documents which are suitable to find the at least one distinguishing property.

The user interface may be arranged for enabling the user to adapt the set of documents found by the document analyzer to obtain an adapted set of documents, and wherein the associating subsystem is arranged for associating the access control policy with the adapted set of documents. This allows the system to take into account fine-tuning choices made by the user. The system may be arranged for, based on the user-made choices, deriving further distinguishing properties or refining the distinguishing properties, based on machine learning techniques, to improve future uses of the system.

The user interface may be arranged for enabling the user to make a change to the at least one distinguishing property found by the property finder, and wherein the document selector is arranged for selecting the set of documents, based on the modified distinguishing property. This enables the user to refine the properties used to select the documents the user does not agree with, for example to correct a property found by the property finder. Such changes can be used to improve the algorithms used in the property finder in future uses, using a machine learning technique, for example.

The change may comprise the removal of one or more of the distinguishing properties from the at least one distinguishing property. For example, if a user thinks that one of the properties is not relevant for him, the user may simply remove that property, so that the removed property will not be used this time for selection of documents.

The topic may comprise a keyword. This allows the document analyzer to use string matching techniques to find the topic as a keyword occurring in a document. Alternatively, the topic may be represented by, for example, an icon which may be displayed on screen, enabling a user to select one of a plurality of graphical representations of topics, for example. Internally, the topic may be represented by a keyword in the system. A topic may also be represented by a collection of keywords, for example words which are synonyms or words which are semantically closely related to each other. The topic may also comprise a document type.

The document analyzer may be arranged for searching for the keyword in the content of the documents. This allows an efficient implementation of the document analyzer.

The document analyzer may be arranged for finding further keywords, based on the content of the documents containing the keywords, and for selecting the set of documents, based on the further keywords. This finding of further keywords may be based on a frequency analysis or on other information retrieval and/or natural language processing techniques, to find further keywords which are related to the keyword originally indicated by the user.

The at least one distinguishing property may comprise a data type or a keyword. These two kinds of properties are highly suitable to implement an accurate and/or efficient selection process.

The property finder may be arranged for applying natural language processing and/or an information retrieval method to the content of the plurality of documents. Such techniques, known in the art per se, may be applied to successfully find a distinguishing property.

The system may comprise an access control subsystem arranged for being configured with the access control policy obtained by the associating subsystem. The access control subsystem, configured with the access control policy, may enforce the access control in the way the user desires.

In another aspect, the invention provides a workstation comprising the system set forth.

In another aspect, the invention provides a method of creating an access control policy, comprising enabling a user to indicate a topic and a set of permissions;

analyzing the content of a plurality of documents to find a set of documents relating to the topic; and associating the set of permissions with the set of documents to obtain an access control policy.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
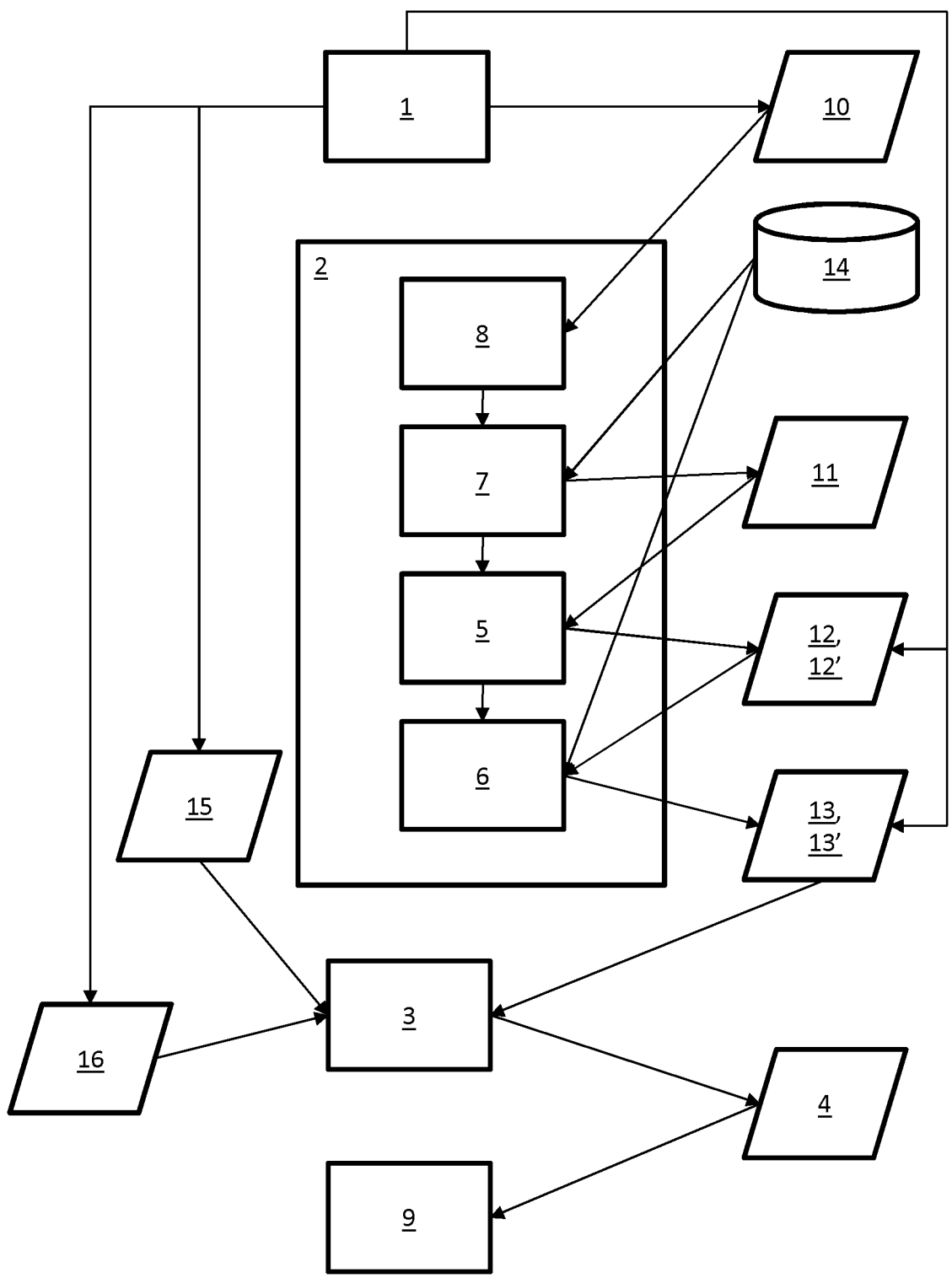
FIG. 1 is a block diagram of a system for creating an access control policy with an access control system.

Information retrieval methods may be based on the term statistics in a collection of textual documents, i.e., using the number of term occurrences in a document (term frequency) and/or in a collection (collection frequency), and the number of documents containing a term. This is explained in Baeza-Yates, R., & Ribeiro-Neto, B. (1999). *Modern Information Retrieval*. Essex, UK: ACM Press (hereinafter: Baeza-Yates et al.). Besides information search, such statistical information, along with available ontologies, can be useful in helping the user to define various properties related to the data collection in question.

Consumers/patients usually have very high-level privacy preferences and are not familiar with the structure of electronic health records (EHRs) and object vocabularies used by EHR systems such as the one of HL-7 described above. They have difficulties in specifying their privacy policies and consent, as there is a large discrepancy between their preferences on the one hand and vocabularies used in access control systems on the other hand. Therefore, there is a need to translate their high-level preferences into machine-readable policies that constrain the use of their health data in a well-controlled, fine-grained manner.

For example, a patient/consumer may want to set up his/her preferences for his/her personal health record (PHR) imported from an electronic medical record from his/her hospital. For example, let us assume that he/she wants to share his/her record with several users, but wants to hide some information, such as the fact that he/she had a certain disease (e.g. a mental disorder, drug abuse, or AIDS).

He/She does not want to review all his/her records in the database one by one and exclude and/or specify permissions for each instance of his/her records in the database that contain the sensitive information. It is neither sufficient to exclude particular data types, as the patient/consumer cannot anticipate all data types and records that might contain the sensitive information. Instead, the patient wants to convey to the IT system in an easy way that he/she wants to hide all the records related to the sensitive information, for example all records from which a third person could understand that the patient/consumer has AIDS. The patient/consumer would like the system to translate this high-level policy (e.g. a keyword, 'AIDS') into a machine-readable access control policy that defines permissions or restrictions at the level of the instances of data types (objects) specified by for example the HL-7 vocabulary. The access control policy generated by the system could be defined at the level of data types. However, it may also be defined at the level of instances of data objects, for example specifying permissions for individual documents. For example, an electronic health record may contain, among other data types, also the 'prescription order' data type, and the electronic health record may have several instances of this data type. It is possible that only one instance of the type 'prescription order' contains the sensitive information, e.g. information related to AIDS. Only this particular instance of the type 'prescription order' is associated with the special permissions relating to AIDS. The other instances of the type 'prescription order' may be associated with a set of permissions generally applying to instances of the type 'prescription order'.

The system and method disclosed herein may be used to translate the consumer/patient input (privacy preference) into a machine-readable access control policy. The consumer input, i.e. privacy preferences, may be in the form of the tuple (user identifier, permission, keyword). For example the tuple (Doctor John Smith, Read, AIDS) would mean that Dr. John Smith can read the consumer's records related to AIDS. The machine-readable policy may be in the form of the tuple (user identifier, permission, data object identifier). The latter tuple would specify a data object to which a user has a particular permission. The techniques disclosed in this description may be used to map a keyword or topic specified by the patient into a set of objects in the electronic health record that contain information related to the keyword.

FIG. 1 illustrates aspects of a system for generating an access control policy. The rectangles (e.g. 1) denote functional units of the system. The parallelograms (e.g. 10) represent data items. The arrows indicate flows of information between the functional units. The division of the functionality among the functional units is presented by way of example only. The system may be implemented at least partly on a computer system. Such a computer system may be implemented as a standalone workstation which has preferably access to an online database. The system can also be implemented on a server and can be provided with a web-based interface or a client-server based user interface. Other implementations are also possible. The common elements of computer systems, such as hard drive, keyboard, display, communications port, and the like, are known to the person skilled in the art and will not be described in further detail herein.

The system may comprise a user interface 1 for enabling one or more users to interact with the system. This interface may be web-based or implemented in another suitable manner. The user interface may have many other user interface elements and provide other functionalities which are not described herein. In this description, only those user interface elements are described which are necessary for a proper understanding of the techniques disclosed herein. The user interface 1 may be arranged for enabling a user to indicate a topic 10 and a set of permissions 15. For example, the user interface may display a list of topics in the form of textual or graphical representations (icons) representing different topics which may be the subject of access control, and enable the user to select one or more topics by clicking on or touching the textual or graphical representations. Alternatively, the user may be presented with a text box in which the user is enabled to type a textual expression, such as one or more keywords or e.g. a phrase. The topic 10 or topics thus obtained may be stored in a temporary memory and/or transmitted via a network to a computer system hosting the document analyzer 2. The set of permissions 15 may be indicated by the user in a similar way, e.g. by enabling the user to select one set of permissions from a list of representations of sets of permissions. Alternatively, the user can be presented with a list of separate permissions and enabled to select one or more of the permissions shown for inclusion in or exclusion from the set of permissions. Alternatively, the user may be enabled to enter the set of permissions in a textual form. Examples of permissions are: permission to read, write, modify, create, delete, print, or forward. The user interface 1 may further be arranged for enabling the user to specify at least one user 16 to whom the set of permissions 15 are to be applied. For example, the at least one user 16 may be a single user, a plurality of specifically specified users, or a group of users. Such a group of users may be defined by their role or by institution, for example. The user interface 1 may further be arranged for enabling the user to specify a plurality of pairs, each pair associating a set of permissions 15 with at least one user 16. These permissions and user pairs may then be associated with a set of selected documents, as will be described hereinafter.

The system may further include a document analyzer 2 for analyzing the content of a plurality of documents 11 to find a set of documents 13 relating to the topic 10. For example, a keyword may be searched in the documents, and all documents having the keyword may be included in the set of documents 13. The plurality of documents 11 may consist of all documents in an electronic health record stored in a patient database 14. However, it is also possible that only the content of a subset of the documents in the electronic health record are analyzed. The document analyzer may perform its task in several ways, which will be elucidated hereinafter.

The system may further include an associating subsystem 3 for associating the set of permissions 15 with the set of documents 13. Moreover, the at least one user 16 to whom the set of permissions 15 is granted may be associated with the set of permissions 15. This way, the access control policy 4 is generated. The access control policy 4 may comprise a tuple (UID, P, OID)=(user ID, permission, object ID). Such a tuple specifies that a user identified by UID is granted permission P in respect of the object (e.g. a document or instance of a document type) identified by OID. For example, a copy of the set of permissions 15 for each user 16 or user group is stored as a set of attributes with each document in the set of documents 13, to form the access control policy 4. Alternatively, the generated tuples (UID, P, OID) may be stored as an access control policy 4, for example in the form of an access control matrix, a set of logical rules, or in XACML format. Such formats in which the access control policy 4 may be represented and/or stored are known to the person skilled in the art per se. The set of documents 13 may also be encrypted by the associating subsystem 3, if the set of permissions so prescribes.

The document analyzer 2 may comprise a data type selector 8 for selecting at least one data type, based on the topic 10. This data type selector 8 may be integrated with the user interface 1, for example in an embodiment in which the user interface 1 displays a list of data types from which the user may select. Alternatively, the user may be enabled to indicate a topic 10, which is translated by the data type selector 8 into one or more relevant data types. This translation step may be based on information stored in an ontology such as SNOMED. This translation, or mapping, can be achieved directly or via a stemming step (known per se from e.g. Baeza-Yates et al., pg. 168) to better handle a free keyword input, i.e., by matching only the word stem instead of the entire freely entered keyword. The mapping may be driven, for example, by the existing ontology (e.g., appropriate SNOMED codes) and/or using the database containing all the data types selected by other customers using the same keyword. The data type selector 8 may also be arranged for searching documents containing the keyword, and selecting document types of the documents containing the keyword. The user interface 1 may be configured for showing the automatically selected data types together with an example of a document of that data type, to enable the user to (de)select data types for further processing.

The document analyzer 2 may further comprise a document pre-selector 7 for selecting, based on the topic 10, the plurality of documents 11 that are analyzed by the property finder 5. For example, the document pre-selector 7 may be arranged for performing a keyword search of one or more keywords relating to the topic 10. For example, the topic 10 may be represented by a keyword itself, and the document pre-selector 7 may be arranged for finding the documents which contain that keyword. Also, additional keywords may be found using an ontology, and documents containing these additional keywords may also be included in the plurality of documents.

In the case that the system comprises the data type selector 8, the document pre-selector 7 may be arranged for selecting a plurality of documents 11 of the selected data type.

The document analyzer 2 may comprise a property finder 5 for analyzing the content of a plurality of documents 11 to find at least one distinguishing property 12 of documents relating to the topic 10. Such a distinguishing property 12 may be the presence of a particular keyword in the content and/or metadata of a document. As the plurality of documents 11 generated by the document pre-selector 7 have at least some content relating to the topic 10, it may be possible to derive from that content properties of documents relating to the topic 10. For example, AIDS is related to some particular medication, e.g. lamivudine, etravirine, tipranavir, and enfuvertide. Since these terms may appear in the plurality of documents 11, the system may conclude that documents including the terms lamivudine, etravirine, tipranavir, and/or enfuvertide are a distinguishing property of documents relating to AIDS, because a third party may conclude that the patient has an AIDS related disease if he knows that these medications are prescribed.

Such a relation between a disease and corresponding medication may be already included in the ontology, but if not, such a relation can be derived from the plurality of documents 11, as there will be some documents in which the diagnosis of a disease is coupled with a prescription of medication. Consequently, the system can learn such associations from the documents. More generally, this may be done using typical lexical and information retrieval algorithms:

Searching for synonyms of the keyword. The synonyms can be found in a general purpose dictionary, but also in a specific medical dictionary that covers medical terminology. Each synonym can be assigned a number representing its relevance with respect to the topic indicated by the consumer.

Searching for the most frequently used terms in the plurality of documents 11 selected by the document pre-selector 7. The most frequently used terms can be selected by using an information retrieval method, based on e.g. term frequency in a document and/or inverse document frequency. For example, number of documents containing the term, such as tf. idf, BM25, language models, see Baeza-Yates et al., Chapter 2: Modeling. In addition, information on term proximity (phrases) can be used for estimating the relevance of terms for the user, using techniques known from e.g. "Term Proximity Scoring for Keyword-Based Retrieval Systems" by Rasofolo, Y., & Savoy, J. in Advances in Information Retrieval (2003). As a result of this stage, a list of keywords (and/or phrases) with the associated probability of relevance may be determined.

Re-evaluation of the top k most relevant terms, using a relevant dictionary, for example a medical dictionary that contains a medical database-specific stopword list and medical term statistics distribution. This step is useful because the term distribution in the medical reports might be significantly skewed in comparison to a general term distribution. As a result, a new relevance score for the top k terms may be determined. It is possible to continue only the l terms with the highest relevance, wherein l<k.

The k and l parameters mentioned above can be specified by the administrator, consumer, or empirically determined, for example.

The user interface 1 may be arranged for displaying the list of l additional keywords and enable the user to select the ones that he/she would like to include in the secondary search. Optionally the relevance of each term should be displayed. Alternatively, the selection of additional keywords is performed automatically and the keywords are forwarded to the document selector 6 without user interaction.

Distinguishing properties other than presence of keywords may also be supported, for example a more complex logical expression involving one or more keywords can be generated (e.g. presence of keyword A, but not keyword B), or properties relating to metadata or attributes of documents. The at least one distinguishing property 12 may also comprise a data type. The property finder 5 may be arranged for applying natural language processing and/or an information retrieval method to the content of the plurality of documents 11.

The document analyzer 2 may further comprise a document selector 6 for selecting the set of documents 13, based on the distinguishing property 12. In the case that the distinguishing property 12 is presence of a keyword, a keyword search may be performed on all documents in the electronic health record. In the case of a logical expression, this logical expression may be evaluated for all documents in the electronic health record.

The document selector 6 may be arranged for performing the additional document search, based on the distinguishing property, for example the selected keywords, in a fashion of a query term expansion (see e.g. "Query Expansion", by Efthimiadis, E. N., 1996, in: Annual Review of Information Systems and Technology (ARIST)). This additional search may be performed using an information retrieval method that might be the same as or similar to the one used in the previous step. However, in this case the complete records may be evaluated based on the selected keywords, using an information retrieval method.

First, the top m records that are the most relevant to the selected keywords may be identified (where the degree of relevance is estimated). These records may be ranked in a descending order with respect to their relevance and, optionally, presented to the user for selection. Afterwards, the relevance of the records may be aggregated based on their association with data types. The list of top n data types may then be presented to the user in descending order. As in the previous step, the choice of m and n can be either empirically determined or pre-selected by a user. The user may be provided with the option to select which data types and/or records he would also like to add to the set of restricted data types. By selecting the data type, the automatic selection of records belonging to that data type can be realized, for example.

The user interface 1 may be arranged for displaying the set of documents 13 found by the document analyzer 2. The user interface may further be arranged for enabling the user to adapt the set of documents 13 to obtain an adapted set of documents 13'. The associating subsystem 3 may be accordingly arranged for associating the set of permissions 15 with the adapted set of documents 13'. Alternatively, the set of documents 13 is processed by the associating subsystem 3 without user intervention.

As mentioned above, the user interface 1 may be arranged for enabling the user to make a change to the at least one distinguishing property 12 found by the property finder 5, and the document selector 6 may be arranged for selecting the set of documents 13, based on the modified distinguishing property 12'.

The system may further comprise an access control subsystem 9 arranged for being configured with the access control policy 4 obtained by the associating subsystem 3. The access control subsystem 9 may be arranged for enforcing the set of permissions 15 on the set of documents 13 and the at least one user 16. Such access control systems are known in the art per se and can be built by the skilled person in view of the present description.

Figure 2:
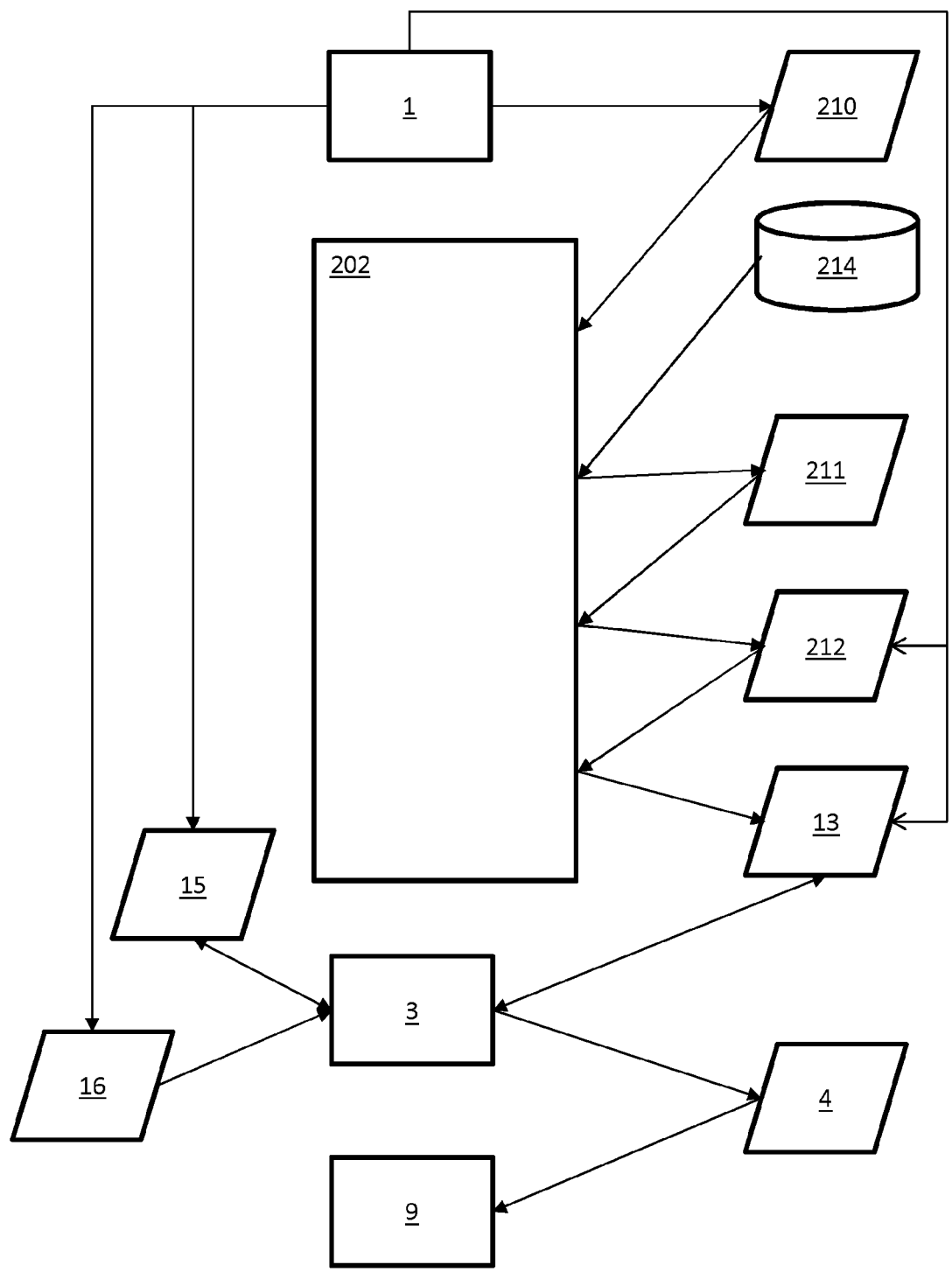
FIG. 2 is a block diagram of another system for creating an access control policy with an access control system.

FIG. 2 illustrates a similar system for generating an access control policy. Only the differences with the system of FIG. 1 are described here. Similar objects have been indicated in FIG. 2 using the same reference numerals. In the system of FIG. 2, the topic comprises a keyword 210. The document analyzer 202 is arranged for searching for the keyword 210 in the content of the documents 214 of an electronic health record, to obtain a plurality of documents 211 containing the keyword 210. The document analyzer 202 may be arranged for finding further keywords 212, based on the content of the documents 211 containing the keyword 210, in a way set forth elsewhere in this description, and for selecting the set of documents 13, based on the further keywords 212.

Figure 3:
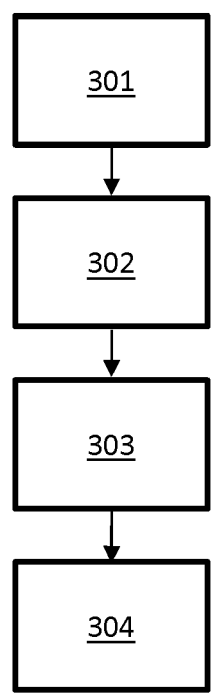
FIG. 3 is a flowchart of a method of creating an access control policy.

FIG. 3 shows a flowchart of a method of creating an access control policy. The method may comprise a step 301 of enabling a user to indicate a topic and a set of permissions. The method may proceed with a step 302 of analyzing the content of a plurality of documents to find a set of documents relating to the topic. The method may proceed with a step 303 of associating the set of permissions with the set of documents to obtain an access control policy. Here the method may terminate. Alternatively, the method may continue with a step 304 of enforcing access to the set of documents according to the associated set of permissions. Variations and extensions of the method can be carried out by the skilled person in view of the description of the system herein. For example, the user may be enabled to indicate a user or users whom are granted the set of permissions. In step 303, the association may be extended such that the set of permissions is associated with both the set of documents and the indicated user or users. The methods and systems described herein may be implemented at least partially in software as a computer program product.

A subset of records (or documents) may be identified in the (consumer) EHRs/PHRs that contains information relating to a consumer-defined topic, e.g. a keyword. This may be done in three steps:

Direct mapping (based on ontology for example): identify the data types that contain the records (e.g. documents) relevant for the consumer privacy preference. Direct mapping may be established between a keyword (such as AIDS) specified by the user in his or her privacy preferences and the data types that contain relevant documents. This mapping can be for example based on an existing ontology (e.g., appropriate SNOMED codes). The data types and/or documents, which are identified to have a relation with the keyword specified by the user, are marked and access to them is restricted as specified in the consumer privacy preferences. It is also possible, for example, to perform a direct search for documents containing the keyword or a keyword relating to the user-specified keyword according to an existing ontology. This way, the step of selecting document types may be omitted.

Extraction of extra keywords: In the second step additional keywords may be extracted from the relevant documents (or data types) identified in the first step. For example, a keyword could be a name of a medicine mentioned in one of the records directly mapped to the originally specified keyword.

Identification of extra records: The rest of the records are searched using the user-defined keyword plus the extra keywords extracted in the second step. This enlists additional data types and/or records that the consumer can use to specify his/her privacy policy.

In addition, relevance (confidence factor) of selected keywords, records, or data types may be calculated in each step and optionally presented on the display to help the user in specifying his/her privacy policy. The threshold and/or top x entities may be fed back to the user to automate or speed-up the specification process. The access control policy defined by the consumer is applied to the identified records.

Note that the previous three steps may involve interaction with the user in all the steps for defining the security policies. However, a subset or all of these steps can be automated, in particular when there is sufficient empirical evidence (of typical user policy selection profiles) and a large enough database of user privacy policies. In such a case, the specification of security policies would be realized with less interaction from the user and a smaller amount of information feed back during various steps. For example, in the last step, only the less relevant data types and most specific records can be shown, while the system will automatically include data types and records whose relevance is higher than the empirically determined threshold.

Figure 4:
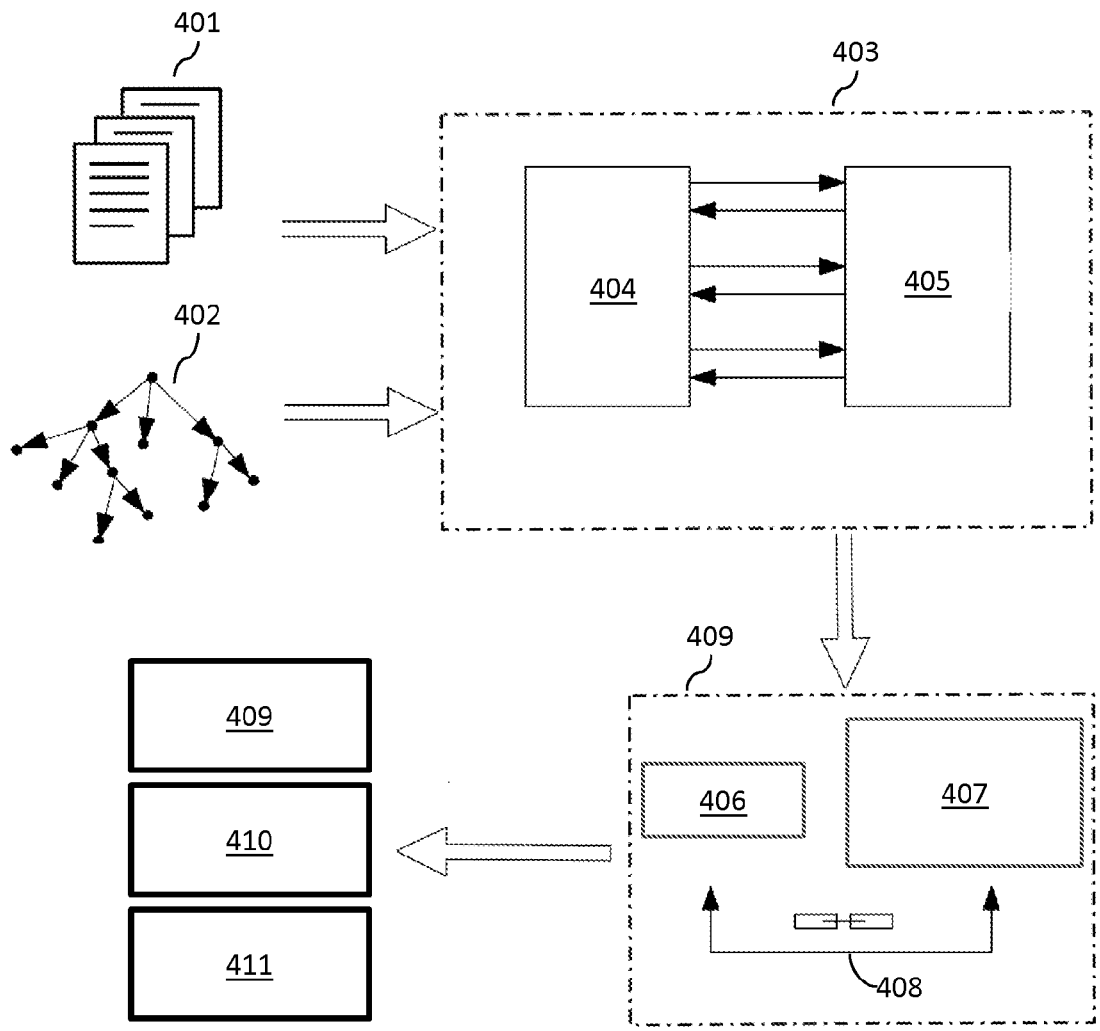
FIG. 4 is a block diagram of an access control system including a system for creating an access control policy.

FIG. 4 shows a diagram with an overview of a context of a system 403 for generating an access policy. Input to the system 403 is an electronic health record containing a plurality of documents 401. A further input to the system 403 is an ontology 402. The system 403 comprises a user interface 405 and a document analyzer 404. As illustrated tentatively by the arrows between the document analyzer 404 and the user interface 405, there may be three stages of interaction: a first indication of a topic by means of e.g. keywords; a first user selection of data types/documents proposed by the document analyzer 404; and a final user selection of data types/documents proposed by the document analyzer 404. The result 409 may comprise a mapping 408 from the original topic/keyword 406 onto a set of data types/documents 407. To create an access control policy, a set of permissions may be associated with the set of documents 407. These associations may be used in several ways, for example by a personal preference manager 409 to store the access control policy and/or the mapping 408 into a personal user profile for future use. This allows the user to more easily apply permissions to documents relating to that keyword. An access control system 410 may be operated under control of the access control policy. A machine learning component 411 may be operative to create general use mappings between keywords and data types/further keywords, based on the mapping 408. These general-use mappings may be the result of mappings 408 produced by different users, and the knowledge incorporated therein may be used to improve the automatic portions of the document analyzer 403, using machine learning techniques known in the art per se. This way, user interaction in the document analyzer 403 may be reduced or totally avoided.

Figure 5:
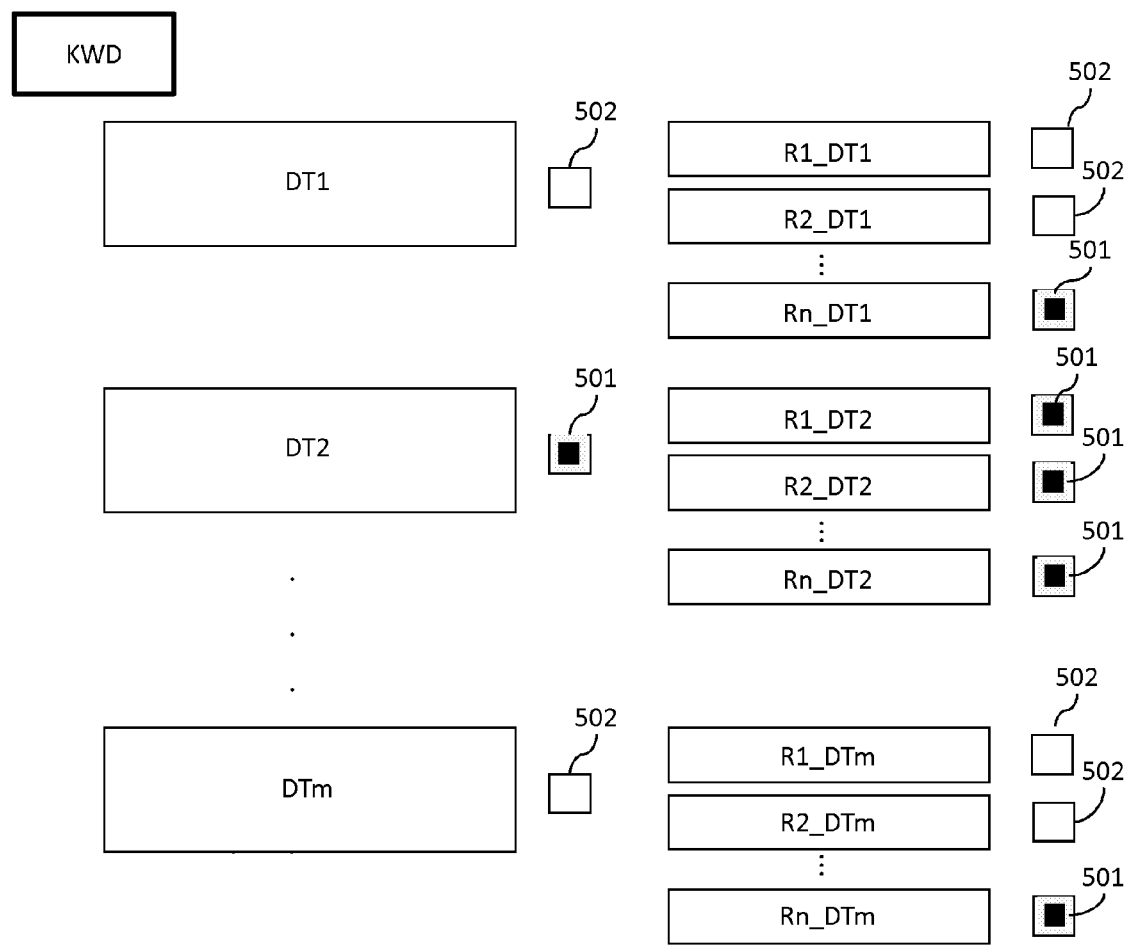
FIG. 5 is a sketch of a user interface used for creating an access control policy.

FIG. 5 is a sketch of a user interface layout which may be generated by user interface 1 which enables a user to select from a number of data types and/or documents. Such an interface layout can be used to enable the user to make a selection in the different interactive steps of the access control policy creation process. At KWD the user-entered keyword or indicated topic may be shown. At DT1, DT2, . . . , DTm, the different data types considered relevant for the keyword/topic may be shown. At R1_DT1, R2_DT1, . . . , Rn_DT2, the documents of data type DT1 are shown. At R1_DT2, R2_DT2, . . . , Rn_DT2, the documents of data type DT2 are shown. At R1$_{13}$ DTm, R2_DTm, . . . , Rn_DTm, the documents of data type DTm are shown. In this way, m data types are shown and n documents for each type. Note that the number of documents shown for each type does not need to be the same for each type. Next to each data type and document, a check box is shown which enables the user to select 501 or deselect 502 that particular data type or document for inclusion in the next processing step. Inclusion of a document type DT2, 501 generally means to automatically include all documents R1_DT2, R2_DT2, . . . , Rn_DT2 of that document type DT2. Such details can be taken care of in the user interface 1. It is possible to omit either the document types DT1, DT2, . . . , DTm or the individual documents Rx_DTy from the user interface in the case that input therefore is not expected at that particular point in the procedure.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for controlling access to medical documents associated with a user in a patient database, comprising:
 a processing device that includes:
  a user interface that receives a topic and a set of permissions from a user;
  a document analyzer that analyzes content of the medical documents associated with the user to find a plurality of documents relating to the topic;

a property finder that analyzes the content of the plurality of documents to find at least one distinguishing property of the documents relating to the topic; and a document selector that selects a set of documents based on the at least one distinguishing property; and wherein the user interface enables the user to select some or all of the set of documents found by the document analyzer; and an associating subsystem that associates the set of permissions with the selected set of documents to obtain an access control policy;

a non-transitory memory element that stores the access control policy for subsequent access control to the set of documents; and an access control subsystem that:

receives an access request for one or more of the medical documents associated with the user from another user, retrieves the access control policy from the memory element, and controls access to each of the one or more medical documents associated with the user based on the access control policy.

2. The system according to claim 1, wherein the document analyzer comprises a document pre-selector that selects, based on the topic, the plurality of documents that are analyzed by the property finder.

3. The system according to claim 2, wherein the document analyzer comprises a data type selector that selects at least one data type, based on the topic; and wherein the document pre-selector selects at least one document based on the at least one selected data type.

4. The system according to claim 1, wherein the user interface enables the user to make a change to the at least one distinguishing property found by the property finder, and wherein the document selector selects the set of documents, based on the modified distinguishing property.

5. The system according to claim 1, wherein the topic comprises a keyword.

6. The system according to claim 5, wherein the document analyzer searches for the keyword in the content of the user's medical documents.

7. The system according to claim 6, wherein the document analyzer finds further keywords, based on the content of the documents containing the keyword, and selects further documents of the set of documents, based on the further keywords.

8. The system according to claim 1, wherein the at least one distinguishing property comprises a data type or a keyword.

9. The system according to claim 1, wherein the property finder applies natural language processing and/or an information retrieval method to the content of the plurality of documents.

10. A method of controlling access to medical records associated with a user in a patient database, comprising enabling the user to indicate a topic and a set of permissions;

analyzing content of the medical documents associated with the user to find a plurality of documents relating to the topic;

identifying at least one distinguishing property of the plurality of documents relating to the topic;

selecting a set of documents from the medical documents associated with the user based on the at least one distinguishing property relating to the topic; and enabling the user to select some or all of the set of documents found by a document analyzer, and associating the set of permissions with the selected set of documents to obtain an access control policy; and storing the access control policy in a non-transitory computer readable memory element to enable subsequent enforcement of the set of permissions with regard to access to the set of documents;

receiving an access request for one or more of the medical documents associated with the user from an other user;

retrieving the access control policy from the memory element; and controlling access to each of the one or more medical documents associated with the user based on the access control policy.

11. A non-transitory computer readable medium that includes one or more computer programs that, when executed by a processor, cause the processor to:

receive a topic and a set of permissions from a user;

search content of medical documents associated with the user to identify a plurality of documents relating to the topic;

analyze the content of the plurality of documents to find at least one distinguishing property of the plurality of documents relating to the topic; and select a set of documents from the medical records associated with the user based on the at least one distinguishing property;

enable the user to select some or all of the set of documents found by a document analyzer, and associate the set of permissions with the selected set of documents to obtain an access control policy; and store the access control policy in a memory element to enable subsequent enforcement of the set of permissions with regard to access to the set of documents;

receive an access request for one or more of the medical documents associated with the user from another user;

retrieve the access control policy from the memory element; and control access to each of the one or more medical documents associated with the user based on the access control policy.

12. The medium of claim 11, wherein the topic comprises a keyword, and the one or more computer programs causes the processor to search for the keyword in the content of the medical documents associated with the user.

13. The medium of claim 12, wherein the one or more computer programs cause the processor to find further keywords, based on the content of the medical documents containing the keyword, and to find the at least one distinguishing property based on the further keywords.

* * * * *